(12) United States Patent
Cossarizza

(10) Patent No.: US 7,604,964 B2
(45) Date of Patent: Oct. 20, 2009

(54) METHOD OF DETERMINING THE COPY NUMBER OF A NUCLEOTIDE SEQUENCE

(75) Inventor: Andrea Cossarizza, Modena (IL)

(73) Assignee: Multigen Holding S.A., Luxembourg (LU)

( * ) Notice: Subject to any disclaimer, the term of this patent is extended or adjusted under 35 U.S.C. 154(b) by 0 days.

(21) Appl. No.: 10/522,405

(22) PCT Filed: Jul. 28, 2003

(86) PCT No.: PCT/NL03/00545

§ 371 (c)(1),
(2), (4) Date: Sep. 30, 2005

(87) PCT Pub. No.: WO2004/011678

PCT Pub. Date: Feb. 5, 2004

(65) Prior Publication Data

US 2006/0105334 A1  May 18, 2006

(30) Foreign Application Priority Data

Jul. 26, 2002  (NL)  .................................. 1021160

(51) Int. Cl.
C12P 19/34  (2006.01)
(52) U.S. Cl. .................................................... 435/91.2
(58) Field of Classification Search ................... None
See application file for complete search history.

(56) References Cited

U.S. PATENT DOCUMENTS 5,389,512 A  2/1995  Sninsky et al.
5,863,736 A  1/1999  Haaland
5,888,740 A  3/1999  Han

FOREIGN PATENT DOCUMENTS

DE  10045521 A  10/2001
EP  0959140 A2  11/1999
EP  1138783 A2  10/2001
WO  WO 99/66075  12/1999
WO  WO 02/097124 A1  12/2002
WO  WO 2004/11678 A1  2/2004

OTHER PUBLICATIONS

Zhang et al., Two variants of quantitative reverse transcriptase PCR used to showdifferential expression of α, β, and γ fibrinogen genes in rat liver lobes, Biochem. J. (1997) 321, 769-775.*
Zhang et al., Differential priming of RNA templates during cDNA synthesis markedly affects both accuracy and reproducibility of quantitative competitive reverse-transcriptase PCR, Biochem. J. (1999) 337, 231-241.*
Ginzinger et al., Gene quantification using real-time quantitative PCR: An emerging technology hits the mainstream, Experimental Hematology 30 (2002) 503-512.*
Ginzinger et al., Measurement of DNA Copy Number at Microsatellite Loci Using Quantitative PCR Analysis, Cancer Research 60, 5405-5409, Oct. 1, 2000.*
Bustin et al., Review, Quantitative real-time RT-PCR—a perspective. Journal of Molecular Endocrinology (2005) 34, 597-601.*
Gibson et al., A novel method for real time quantitative RT-PCR, Genome Res. 1996, 6: 995-1001.*
Reischer, G. H. et al. "A Qualitative Real-Time PCR Assay for the Highly Sensitive and Specific Detection of Human Faecal Influence in Spring Water from a Large Alpine Catchment Area". *Letters in Applied Microbiology*, 44:351-356 (2007).
Winer, J. et al. "Development and Validation of Real-Time Quantitative Reverse Transcriptase-Polymerase Chain Reaction for Monitoring Gene Expression in Cardiac Mycocytes in Vitro". Analytical Biochemistry, 270:41-49 (1999).
Georgieva, S. G. et al. "A Review of the Internet Site 'Practical Molecular Biology'". *Molecular Biology*, 35:961-964 (2001). Translated from *Molekulyarnaya Biologiya*, 35:1116-1119 (2001).

* cited by examiner

*Primary Examiner*—Kenneth R. Horlick
*Assistant Examiner*—Mark Staples
(74) *Attorney, Agent, or Firm*—Browdy and Neimark, PLLC

(57) ABSTRACT

The invention relates to a method of determining of accurately determining the copy number of a nucleotide sequence I in a sample using an amplification technique, such as PCR. In addition, a second nucleotide sequence II is also measured and calibration curves for each are made, from which the relative copy number CN can be determined. According to the present invention, accuracy is improved by performing multiple amplifications in a single well using real time PCR.

28 Claims, 5 Drawing Sheets

METHOD OF DETERMINING THE COPY NUMBER OF A NUCLEOTIDE SEQUENCE

The present invention relates to a method of determining the copy number of a nucleotide sequence I in a sample using an amplification technique, said method comprising the steps of
1) adding nucleotides, primers, polymerase and any further reagents, if any, required for the amplification technique used to the sample,
2) performing one or more amplification cycles to amplify the nucleotide sequence I for which the copy number has to be determined;

where the sample contains a chromosomal second nucleotide sequence II, and
a) the first nucleotide sequence I is amplified,
b) the second nucleotide sequence II is amplified,
c) a third nucleotide sequence I' corresponding to the first nucleotide sequence I and present in a control sample is amplified at various dilutions, and
d) a fourth nucleotide sequence II' corresponding to the second nucleotide sequence II and present in a control sample is amplified at various dilutions, where the ratio of the concentrations of nucleotide sequence I' and II' is known where the amplifications of the third and fourth nucleotide sequences I' and II' at various dilutions allows standard curves $SC_i$ with i being I or II to be made, the concentrations of I and II are determined by using the respective standard curve $SC_i$, and the relative concentrations allows the relative copy number CN of sequence I (versus nucleotide sequence II) to be determined using the formula $$CN = \frac{[I]_{SC_{I'}}}{[II]_{SC_{II'}}}$$

where

CN is the relative copy number of I over II in the sample;
$[I]_{SC_{I'}}$ is the concentration of I determined using standard curve $SC_{I'}$; and
1) $[II]_{SC_{II'}}$ is the concentration of II determined using standard curve $SC_{II'}$.

Most eukaryotic diploid cells contain two copies of a single gene; one on each chromosome of a pair of chromosomes. The chromosomes of a pair of chromosomes being derived from each parent, the genes may be different and, for example, one of them may result in a abnormal protein. Thus, the number of functional genes is not necessarily 2 in an eukaryote, and can be 1 or even 0. While often genes are present in one copy per chromosome of a particular pair of chromosomes, some genes are present in multiple copies, for example in tandem repeat sequences. Another exception to the general rule of 2 copies per cel is mitochondrial DNA. A cell contains many mitochondria, the number being dependant on the type of cell. But even for a particular cell type, the number of mitochondria may vary. Typical numbers are between 100 and 1000 mitochondria per cell, and each mitochondrion contains several copies of mitochondrial DNA. In addition, the typical copy number is not necessarily equal to larger than 2 per cell. Some nucleotide sequences are very rare among cells (despite being of one and the same subject, such as a human being). This is, for example, after gene rearrangement. This is, for example, the case with antibody producing cells (B-lymphocytes) or receptor-carrying T-lymphocytes. Of a large number of lymphocytes, only a few will contain a particular nucleotide sequence defining the variable region of a particular antibody (or of the T-cell receptor), capable of recognizing a particular antigen. In the art, a need exists to reliably determine the copy number of a nucleotide sequence, which may comprise the nucleotide sequence of a gene or part thereof. A method according to the preamble is known in the art.

A method according to the preamble is known disclosed by Kwok et al in U.S. Pat. No. 5,389,512.

The object of the present invention is to improve this method for reliably determining the copy number of a nucleotide sequence even if it is present in extreme amounts, such as lots of copies per cell or only few copies per many cells. In addition, an object of the present invention is to provide a method which has reduced sensitivity to the efficiency with which DNA was extracted from the cells containing a nucleotide sequence I for which the copy number has to be determined.

To this end, the method according to the present invention is characterized in that
at least one pair of amplification reactions chosen from i) a) and b), and ii) c) and d) is performed in a single container and monitored spectrophotometrically during amplification, and
the third nucleotide sequence I' and fourth nucleotide sequence II' resides on a single vector.

This allows for a more accurate measurement of relative or absolute copy numbers of nucleotide sequence I. Suitable spectrophotometrical methods are known in the art. More specifically, such methods rely on internal probes for real time measurements, for example real time PCR. Internal probes are known in the art, and are disclosed by, for example, Winer et al (Anal. Biochem 270, pp. 41-49 (1999)). Measurements can be done either continuously, or after finishing an amplification cycle. While specific reference is made to standard curves, it goes without saying that this can be done using computational methods without an actual graph being made. Hence, in the present application the phrase "making a standard curve" involves any method using at least two reference points to determine a (relative) concentration. Generally, all amplifications will be performed substantially at the same time. By performing multiple amplifications in one container, the room for error is reduced. The method according to the invention is not only highly accurate, but it is also very efficient if performed for multiple samples. That is, for each nucleotide sequence I for which it is desired to determine the copy number, only a single standard curve $SC_{II'}$ has to be made. With respect to the term "corresponding" as used in the present invention in conjunction with nucleotide sequences, this is intended to mean that the nucleotide sequences I and I' (and II and II'), or more specifically the nucleotide sequence of one and the complementary sequence of the other, are capable of hybridizing under stringent conditions. If the sequences I and I' (and II and II') do not have the same length, the shortest of the two is preferably at most 50% shorter, more preferably at most 30% shorter.

The third nucleotide sequence I' and fourth nucleotide sequence II' residing on the same vector allows their ratio to be constant and exactly known (for example 1:1). This allows for the most accurate measurements possible. It is possible to subject the vector containing both nucleotide sequence I' and II' to a digestion using one or more restriction enzymes, optionally followed by purification, to yield a linear molecule containing both both nucleotide sequence I' and II', and using this molecule for the amplifications required for the standard curves.

In the present application, a vector is understood to be any nucleotide sequence consisting of or containing the nucleotide sequence(s) to be amplified. When present on a vector capable of being replicated in vitro or in vivo, it is easy to obtain that particular nucleotide sequence in desired quantities. It is also very easy to determine the DNA concentration and hence the copy number of the nucleotide sequence per volume. A vector capable of replication or being replicated may be any such vector known in the art, such as a plasmid, a cosmid, a virus etc. If, according to a favourable embodiment, the third nucleotide sequence I' resides on first vector and the fourth nucleotide sequence II' resides on a second vector, the vectors can be used (or mixed) at any desired ratio to accommodate expected differences in copy number in the sample.

Douek et al (Nature 396, pp. 690-695 (1998)) describe a method for detecting the products of the rearrangements of T-cell receptors (TREC) using a semi-quantitative assay. For determining the amount of TREC in a given sample, a known amount of a DNA competitor are prepared. Then, an amount of sample DNA containing the nucleotide sequence to be determined are added to the tube. A PCR amplification reaction is carried out in the presence of radiolabeled deoxynucleotide. Subsequently, the resulting amplification products are run on a gel to separate the sample DNA PCR product from the competitor DNA product. After autoradiography, the amount of nucleotide sequence to be determined is calculated using densitometric analysis from the ratio between a band of competitor DNA and a band of the sample DNA. The result is expressed as the number of copies of TREC per microgram total DNA. To achieve an acceptable accuracy, 4 tubes containing scalar amounts of competitor DNA are used, to which fixed amounts of sample DNA are added. The disadvantage of this method is that when DNA is extracted from cells, it must be assumed that this is all the DNA present in the cells. That is, it is assumed that no cell escaped lysis and all DNA present in the cells was extracted and isolated. This is not necessarily the case. Another disadvantage of this method is that it is sensitive to differences in amplification efficiency.

The European patent publication EP 0 959 140 discloses a method and apparatus for determining quantities of nucleic acid sequences in samples using standard curves and amplification ratio estimates. A plurality of standard samples each containing a known quantity of a nucleic acid control sequence, and a test sample containing a known quantity of the nucleic acid control sequence plus a nucleic acid sequence in an unknown concentration, are subjected to an amplification reaction. The concentration of the nucleic acid present in an unknown concentration in the test sample is determined.

The European patent publication EP 1 138 783 discloses a method for the quantification of a nucleic acid in a test sample, by determining the amplification efficiency under defined conditions, and performing the quantification of said nucleic acid under the same defined conditions, allowing correction of the concentration determined for said nucleic acid.

According to a preferred embodiment the absolute copy number is determined by multiplying the copy number CN by the absolute copy number of sequence II per cell.

For several nucleotide sequences II the number of copies of per cell is known. An example is, for example, the gene coding for heat shock protein 70, or Fas Ligand (CD178), which are known to be present with two copies per cell (i.e. the absolute copy number of hsp 70=2). Many nucleotide sequences of genes are very suitable because they generally are present in a known number of copies in every cell of the species from which the DNA is derived. The efficiency with which DNA material is extracted from the cells is not important (although, in case nucleotide sequence I is on a different molecule as nucleotide sequence II, it is important that they are extracted with the same efficiency). Hence, this embodiment allows determination of the absolute copynumber of the nucleotide sequence I per cell.

According to a preferred embodiment, at least two different third nucleotide sequences I' for measuring a corresponding number of different first nucleotide sequences I reside on a single vector.

In other words, a single vector, requiring its concentration to be determined only once, can carry multiple third nucleotide sequences I', which allows, for example, the copy numbers of many different genes to be determined.

Preferably, the sequence of the first nucleotide sequence I is the same as the third nucleotide sequence I'.

This strongly reduces errors due to differences in amplification efficiencies between I and I'. Nevertheless, small differences in nucleotide sequence are generally allowed, although changes at locations where the probe used for detecting the concentration of the nucleotide sequence are best avoided. In other word, it is highly preferred if the probe is a perfect match for the sequence where it is intended to bind.

Similarly, it is preferred that the sequence of the second nucleotide sequence II is the same as the fourth nucleotide sequence II'.

While the present invention is described with reference to DNA, the present invention also applies to the determination of the number of RNA sequences present in a cell. Use can be made of methods known in the art to multiply RNA, for example by preparing cDNA. This application does not attempt to teach an interested layman how to become a person skilled in the art, for which reason the layman is referred to general text books and in particular to a proper university to learn the required techniques that a person skilled in the art knows how to apply these techniques to work the present invention.

BRIEF DESCRIPTION OF THE DRAWINGS

The present invention will now be illustrated with reference to the drawings where.

Figure 1:
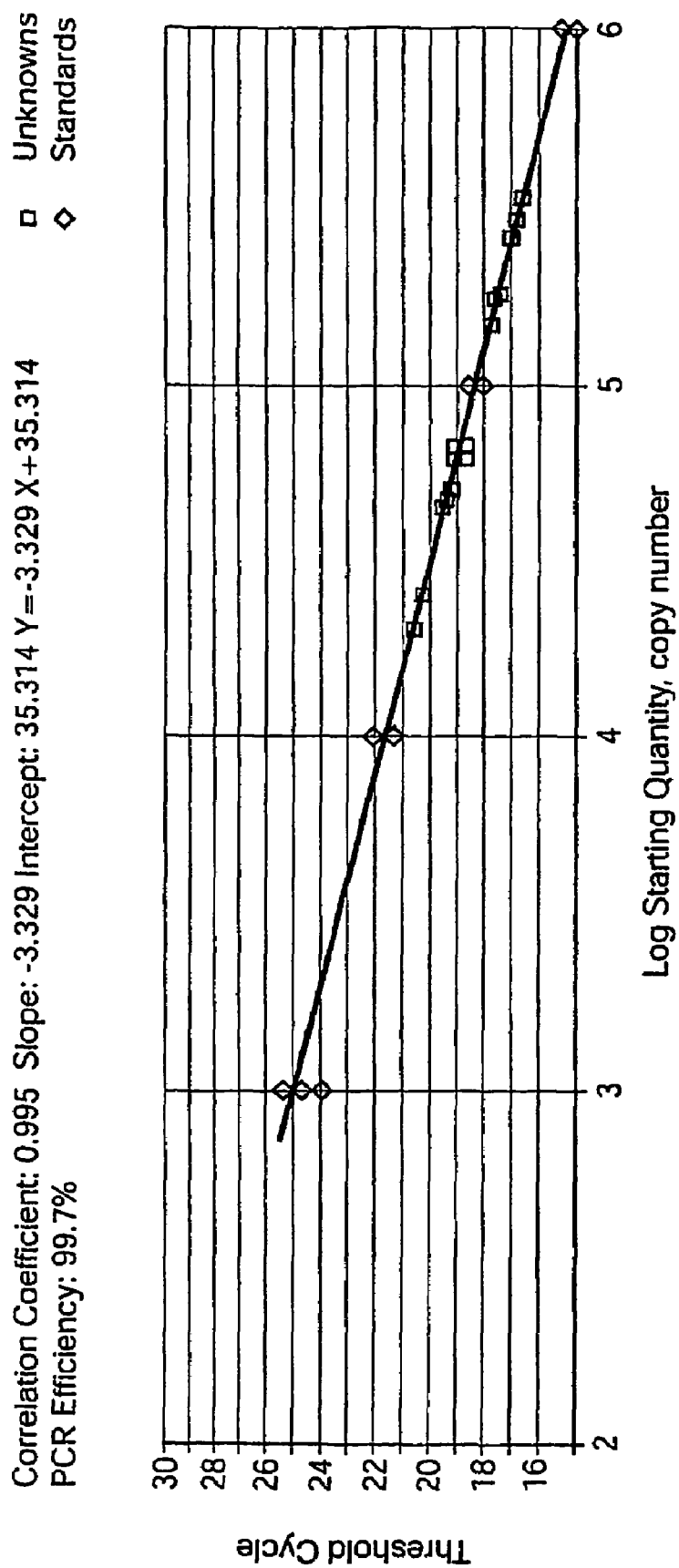
FIG. 1 represents a standard curve for an mtDNA sequence I' (diamonds) plus data for nucleotide sequence I (squares)

The method according to the invention will be illustrated using two Examples. The first relates to the quantitive analysis of mitochondrial DNA (mtDNA) and demonstrates the technique for determining multiple copies per cell. The second Example demonstrates the quantitative determination of a fractional copy number of a particular nucleotide sequence per cell.

EXAMPLE 1

Materials and Methods

Primers

The nucleotide sequence I (mtDNA) was a stretch having a length of 102 nucleotides, and corresponds to part of the enzyme NADH dehydrogenase as coded for by mtDNA. Amplification of nucleotide sequence I was performed using a set of primers, each having a length of 21 nucleotides and synthesized using standard procedures. The sequences of both primers were checked to be unique for human mtDNA using Blast software, through the NCBI site at NIH Worldwide web URL: ncbi.nlm.nih.gov/blast/.

The nucleotide sequence II (nuclear DNA) serving as a reference, was a stretch having a length of 104 nucleotides and part of the FasL gene, which comes with two copies per human cell. Amplification of nucleotide sequence II was performed using a set of primers, each having a length of 21 and 24 nucleotides respectively.

Probes

To monitor the progress of amplification, a probe was used for nucleotide sequence I, the probe having a length of 23 nucleotides, having a FAM (carboxy fluorescein) fluorescent probe at the 5' end and a BLACKHOLE QUENCHER1™ group at the 3' end. This probe, and all others in this application, 10 was ordered commercially with MWG, Ebersberg, Germany. The sequence of the probe was checked to be unique for human mtDNA using Blast software, through the NCBI site as mentioned above.

The probe used for nucleotide II had a length of 22 nucleotides and contained TEXAS RED™ as the fluorescent label and a BLACKHOLE QUENCHER2™ group at the 3' end (MWG).

DNA isolation

DNA was isolated from HL60, a promyelocytic leukaemia cell line, using a DNA isolation kit from Qiagen, Hilden, Germany according to the instructions of the manufacturer.

Control

A vector was constructed, using pGEM-11Z (Promega) containing the sequences I' and II' head to tail, using standard genetic engineering techniques, as all too familiar from Sambrook et al. (Molecular cloning. A lab manual. (1989)) in $E.\ coli$. The nucleotide sequences I' and II' were identical to their respective I and II counterparts, and present on the vector in a highly defined 1:1 ratio.

The absolute concentration of the controls was done using limiting dilution assays (Sambrook).

Amplification

Amplification was performed using an ICYCLER® Thermal cycler (BioRad, Hercules, Calif., USA) using standard procedures. The amplification is performed in plates having 96 wells. This instrument allows monitoring of fluoresence in up to 4 different channels. In short, one cycle of denaturation (95° C. for 6 min) was performed, followed by 45 cycles of amplification (94° C. for 30 s, 60° C. for 60 s). The amplification was performed in a mix that consisted of: Promega PCR buffer 1× (Promega, Madison, Wis., USA), 3.0 mM $MgCl_2$, 400 pmol of primers for mtDNA, 0.2 mM dNTP and 2 U of Taq polymerase (Promega). In accordance with the invention, the amplification for both nucleotide sequences I and II were performed in a single well, and the same is true for nucleotide sequences I' and II' (for determining the standard curves). Data were analysed using the software of the ICYCLER®.

The standard curves were made by introducing a known number of copies of vector per well.

Amplification experiments were performed in triplicate.

RESULTS

Figure 2:
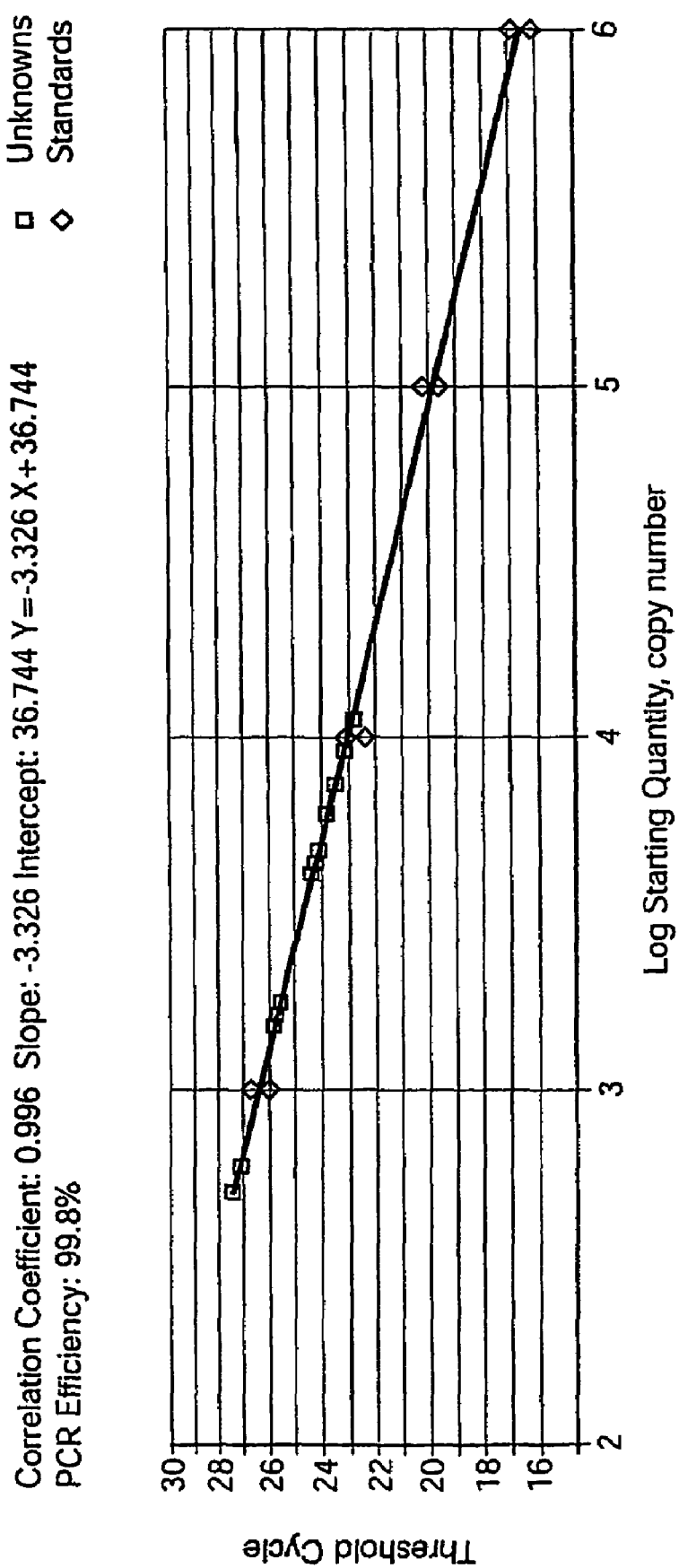
FIG. 2 represents a standard curve for a nuclear DNA sequence II' (diamonds) plus data for nucleotide sequence II (squares)

FIG. 1 shows the standard curve for nucleotide sequence I' and FIG. 2 shows the standard curve for the nucleotide sequence II' based on FasL. Note the excellent correlation coefficients of 0.995 and 0.996 respectively, indicating the excellent accuracy of the method according to the invention. Using these curves, the concentration of nucleotide sequences I and II (shown as squares in FIGS. 1 and 2) were determined. As it is known that the nucleotide sequence for FasL (and more specifically for the probe for nucleotide II/II') is resent with two copies per cell, the number of copies of nucleotide sequence I per cell is twice as high, i-e. 160.

EXAMPLE 2

Basically, the same method was used as described in Example 1, except that the nucleotide sequence I corresponded to part of the sequence of the delta locus of the T-cell receptor. The method was used to determine the number of copies of TREC per cell, in particular peripheral lymphocytes in blood, in three age groups (healthy humans of 20, 60 or 100 years. The number of people were respectively 16 (10), 17 (10), and 21 (17), with the number of women between parentheses)

Figure 3:
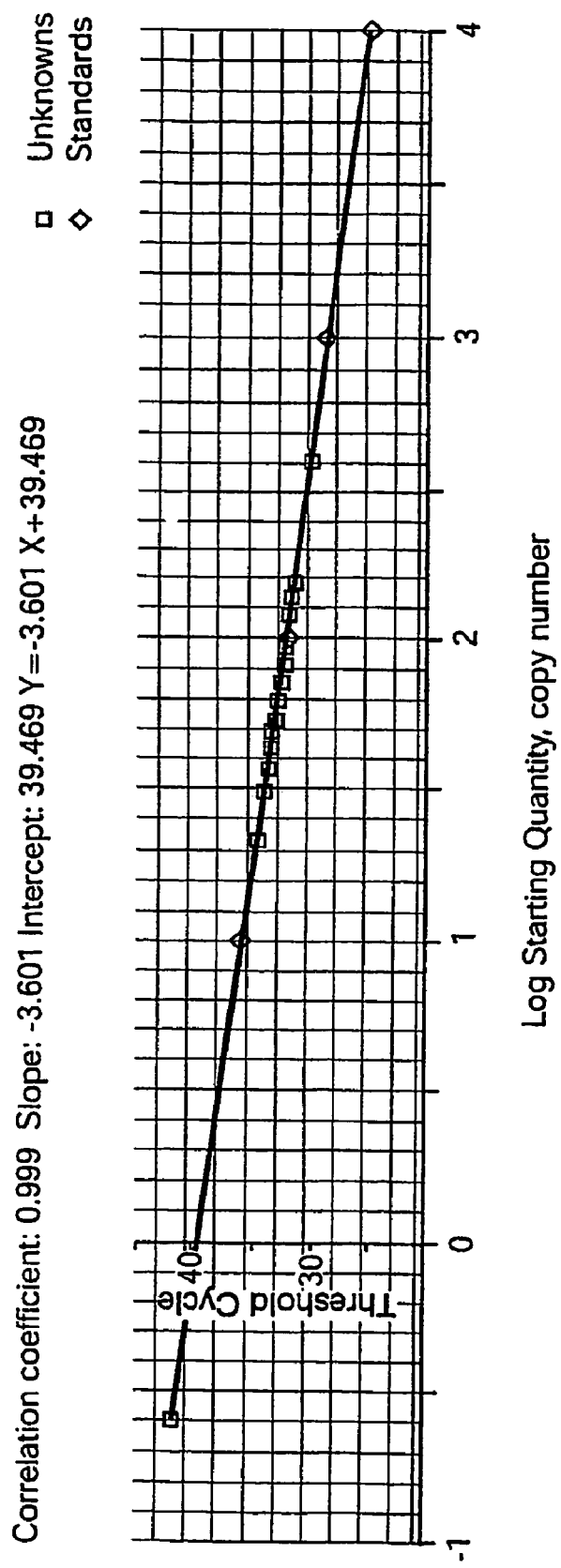
FIG. 3 represents a standard curve for a nuclear DNA sequence II (diamonds) plus data for nucleotide sequence I (squares)
Figure 4:
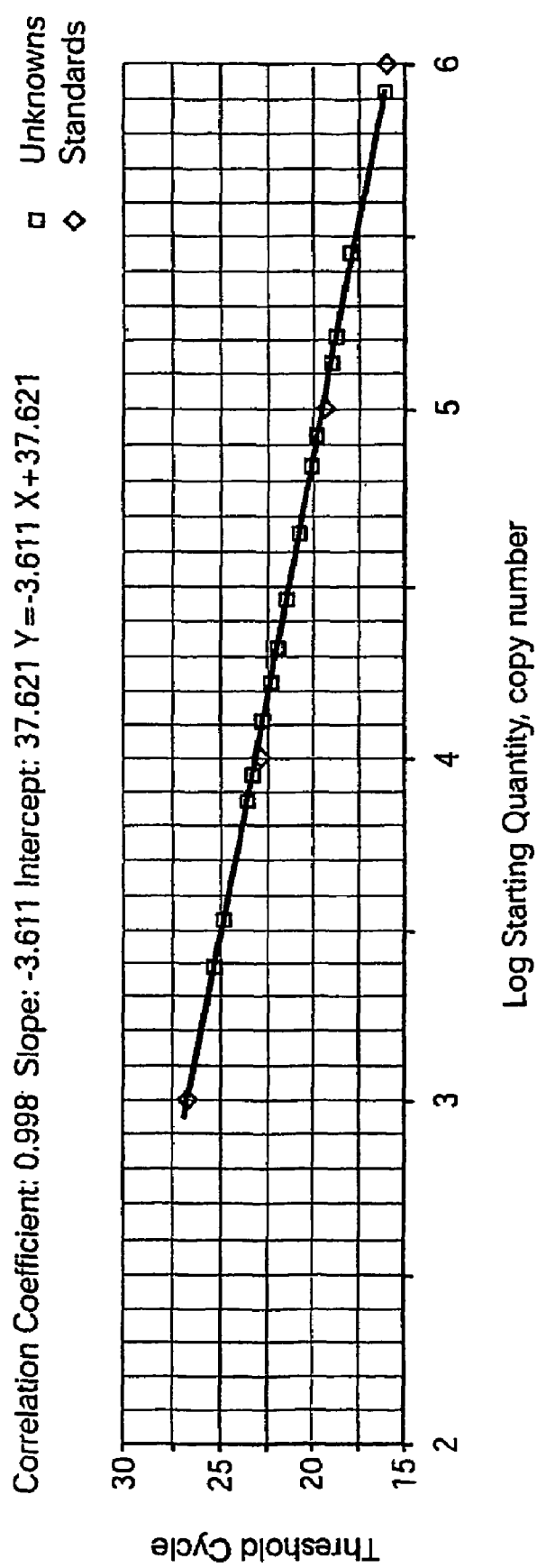
FIG. 4 represents a standard curve for a nuclear DNA sequence II' (FasL) (diamonds) plus data for nucleotide sequence II (squares)

The standard curves for nucleotide sequence I' and II' are shown in FIGS. 3 and 4 respectively. The following correlation coefficients obtained were: 0.999 and 0.998.

Figure 5:
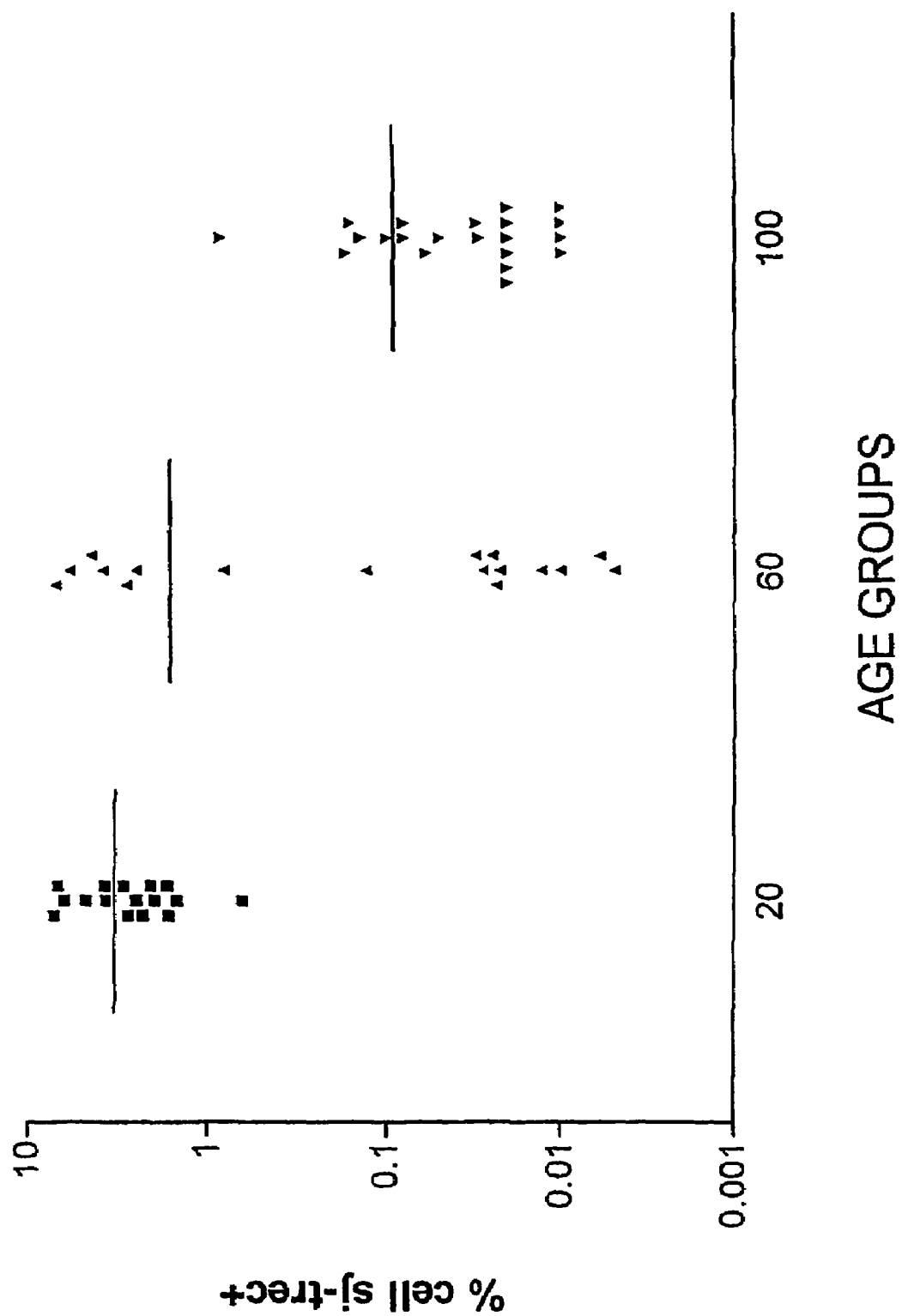
FIG. 5 shows the effect of age on the numbers of copies of TREC in peripheral lymphocytes (percentage of lymphocyte cells expressing TREC).

FIG. 5 shows that the number of copies of TREC decreases with age (averages per age group shown as a horizontal line) from about 3.2 to 0.1 per 100 cells.

While particularly beneficial for the method according to the present invention in view of the fact that spectrophotometrical methods allow simulaneous detection of multiple labels, it is possible to perform an amplification reaction using any known amplification technique, where the third nucleotide sequence I' and fourth nucleotide sequence II' resides on a single vector and the amplifications of each of I' and II' are performed in separate containers, such as separate wells. The application covers this possibility as well. Such amplification techniques comprise, apart from the ones mentioned above, CP (Cycling Probe Reaction), bDNA (Branched DNA amplification), SSR (Self-Sustained Sequence Replication), SOA (Strand Displacement Amplification), QBR (Q-Beta Replicase), Re-AMP (Formerly RAMP), NASBA (Nucleic Acid Sequence Based Amplification), RCR (Repair Chain Reaction), LCR (Ligase Chain Reaction), TAS (Transorption Based Amplification System), and HCS (amplifies ribosomal RNA).

The invention claimed is:

1. A method of determining the relative copy number (CN) of a first nucleotide sequence I (NucSeqI) in a test sample using an amplification technique, said method comprising the steps of:
   (1) adding to the test sample that comprises NucSeqI and a chromosome-derived second nucleotide sequence II (NucSeqII), the following ingredients:
      nucleotides,
      primers,
      polymerase, a first probe specific to NucSeqI comprising a first fluorophore and a quencher, and/or a second probe specific to NucSeqII comprising a second fluorophore and a quencher wherein the first fluorophore and the second fluorophore are different; and optionally any additional reagents required for amplification, (2) carrying out the following amplification steps in one or more amplification cycles:
  (a) amplifying NucSeqI in said test sample,
  (b) amplifying NucSeqII in said test sample,
  (c) in a control sample, to which said ingredients of (1) are added, amplifying at multiple dilutions a third nucleotide sequence I' (NucSeqI') corresponding to NucSeqI to which said first probe is also specific, in the presence of said first probe,
    wherein the relationship of NucSeqI and NucSeqI' is defined as
    (A) NucSeqI hybridizes to the complement of NucSeqI', and
    (B) NucSeqI' hybridizes to the complement of NucSeqI, both under stringent hybridization conditions, and, if NucSeqI and NucSeqI' differ in length, the shorter of the two is at most 30% shorter than the other; and
  (d) in a control sample, to which said ingredients of (1) are added, amplifying at multiple dilutions a fourth nucleotide sequence II' (NucSeqII') corresponding to NucSeqII to which said second probe is also specific, in the presence of said second probe,
    wherein the relationship of NucSeqII and NucSeqII' is defined as
    (A) NucSeqII hybridizes to the complement of NucSeqII', and
    (B) NucSeqII' hybridizes to the complement of NucSeqII, both under stringent hybridization conditions, and, if NucSeqII and NucSeqII' differ in length, the shorter of the two is, at most, 30% shorter than the other;
  wherein
    (i) NucSeqI' and NucSeqII' are both localized on a single vector in which the ratio of NucSeqI' to NucSeqII' is known,
    (ii) standard curves $SC_I$ and $SC_{II}$ comprising at least two reference points are generated by amplification of NucSeqI' and NucSeqII', respectively, at multiple dilutions, wherein the starting quantity, concentration or dilution of NucSeqI' and NucSeqII' is known, and
    (iii) at least one pair of amplification reactions (a) and (b) or (c) and (d) is performed in a single container and monitored by fluorescence during amplification;

(3) determining the results of the amplifications of step (2) expressed as threshold cycle (Ct) as a function of said starting quantity, concentration or dilution;

(4) obtaining from the results in step (3) the following values:
  (i) "Conc-$I_{SCI}$" which is the concentration, quantity or dilution in the test sample of NucSeqI determined from standard curve $SC_I$; and
  (ii) "Conc-$II_{SCII}$" which is the concentration, quantity or dilution in the test sample of NucSeqII determined from standard curve $SC_{II}$,
  which standard curves express threshold cycle as a function of said starting concentration, quantity or dilution; and (5) determining from the values obtained in step (4) the relative CN of NucSeqI with respect to NucSeqII by the formula:

$$\text{Relative } CN = \frac{\text{Conc} - I_{SCI}}{\text{Conc} - II_{SCII}}$$

thereby determining the relative CN of NucSeqI in said test sample.

2. A method according to claim 1, wherein at least two different NucSeqI' sequences, used for measuring a corresponding number of different NucSeqI sequences, are localized on a single vector.

3. A method according to claim 1 wherein the sequences of NucSeqI and NucSeqI' are the same.

4. A method according to claim 1 wherein the sequences of NucSeqII and NucSeqII' are the same.

5. A method according to claim 2 wherein the sequences of NucSeqI and the NucSeqI' are the same.

6. A method according to claim 2 wherein the sequences of NucSeqII and the NucSeqII' are the same.

7. A method according to claim 3 wherein the sequences of NucSeqII and the NucSeqII' are the same.

8. A method according to claim 5 wherein the sequences of NucSeqII and the NucSeqII' are the same.

9. A method according to claim 1, wherein the test sample is derived from cells.

10. A method according to claim 9, wherein an absolute CN of NucSeqII per cell is known.

11. A method for determining the absolute CN of a nucleotide sequence NucSeqI in a test sample, comprising:
  (a) determining the relative CN using the method of claim 10, and
  (b) multiplying the relative CN by the absolute CN of NucSeqII per cell.

12. A method according to claim 11, wherein at least two different NucSeqI' sequences, used for measuring a corresponding number of different NucSeqI, are localized on a single vector.

13. A method according to claim 11 wherein the sequences of NucSeqI and the NucSeqI' are the same.

14. A method according to claim 11 wherein the sequences of NucSeqII and the NucSeqII' are the same.

15. A method according to claim 12 wherein the sequences of NucSeqI and the NucSeqI' are the same.

16. A method according to claim 15 wherein the sequences of NucSeqII and the NucSeqII' are the same.

17. A method according to claim 12 wherein the sequences of NucSeqII and the NucSeqII' are the same.

18. A method according to claim 13 wherein the sequences of NucSeqII and the NucSeqII' are the same.

19. A method according to claim 10, wherein at least two different NucSeqI' sequences used for measuring a corresponding number of different NucSeqI are localized on a single vector.

20. A method according to claim 10, wherein the sequences of NucSeqI and the NucSeqI' are the same.

21. A method according to claim 10 wherein the sequences of NucSeqII and the NucSeqII' are the same.

22. A method according to claim 19 wherein the sequences of NucSeqII and the NucSeqII' are the same.

23. A method according to claim 20 wherein the sequences of NucSeqII and the NucSeqII' are the same.

24. A method of determining the relative CN of a first nucleotide sequence I (NucSeqI) in a test sample using an amplification technique, said method comprising the steps of:
(1) adding to the test sample that comprises NucSeqI and a second nucleotide sequence II (NucSeqII), the following ingredients:
nucleotides,
primers,
polymerase,
a first probe specific to NucSeqI comprising a first fluorophore and a quencher, and/or a second probe specific to NucSeqII comprising a second fluorophore and a quencher, wherein the first fluorophore and the second fluorophore are different; and optionally
any additional reagents required for amplification,
(2) carrying out the following amplification steps in one or more amplification cycles:
(a) amplifying NucSeqI in said test sample,
(b) amplifying NucSeqII in said test sample,
(c) in a control sample, to which said ingredients of (1) are added, amplifying at multiple dilutions a third nucleotide sequence I' (NucSeqI') corresponding to NucSeqI to which said first probe is also specific in the presence of said first probe,
wherein the relationship of NucSeqI and NucSeqI' is defined as
(A) NucSeqI hybridizes to the complement of NucSeqI', and
(B) NucSeqI' hybridizes to the complement of NucSeqI, both under stringent hybridization conditions, and, if NucSeqI and NucSeqI' differ in length, the shorter of the two is at most 30% shorter than the other; and
(d) in a control sample, to which said ingredients of (1) are added, amplifying at multiple dilutions a fourth nucleotide sequence II' (NucSeqII') corresponding to NucSeqII to which said second probe is also specific, in the presence of said second probe,
wherein the relationship of NucSeqII and NucSeqII' is defined as
(A) NucSeqII hybridizes to the complement of NucSeqII', and
(B) NucSeqII' hybridizes to the complement of NucSeqII, both under stringent hybridization conditions, and, if NucSeqII and NucSeqII' differ in length, the shorter of the two is, at most, 30% shorter than the other;
wherein
(i) NucSeqI' and NucSeqII' are both localized on a single vector in which the ratio of NucSeqI' to NucSeqII' is known,
(ii) standard curves $SC_I$ and $SC_{II}$ comprising at least two reference points are generated by amplification of NucSeqI' and NucSeqII', respectively, at multiple dilutions, wherein the starting quantity, concentration or dilution of NucSeqI' and NucSeqII' is known, and
(iii) at least one pair of amplification reactions (a) and (b) or (c) and (d) is performed in a single container and monitored by fluorescence during amplification;
(3) determining the results of the amplifications of step (2) expressed as threshold cycle (Ct) as a function of said starting quantity, concentration or dilution;
(4) obtaining from the results in step (3) the following values:
(i) "Conc-$I_{SCI}$" which is the concentration quantity or dilution in the test sample of NucSeqI determined from standard curve $SC_I$; and
(ii) "Conc-$I_{SCI}$" which is the concentration quantity or dilution in the test sample of NucSeqII determined from standard curve $SC_{II}$, which standard curves express threshold cycle as a function of said starting concentration quantity or dilution; and
(5) determining from the values obtained in step (4) the relative CN of NucSeqI with respect to NucSeqII by the formula:

$$\text{Relative } CN = \frac{\text{Conc} - I_{SCI}}{\text{Conc} - II_{SCII}}$$

thereby determining the relative CN of NucSeqI in said test sample.

25. The method of claim 1 wherein the quantity in the test sample in step (4) is the number of copies of NucSeqI or NucSeqII obtained from the respective standard curves in which the quantity or relative dilution of NucSeqI' or NucSeqII', expressed as copy number, is plotted on the X-axis.

26. The method of claim 1 wherein the concentration in the test sample in step (4) is the molar or weight concentration of NucSeqI or NucSeqII obtained from the respective standard curves in which the concentration or relative dilution of NucSeqI' or NucSeqII' is plotted on the X-axis.

27. The method of claim 24, wherein the quantity in the test sample in step (4) is the number of copies of NucSeqI or NucSeqII obtained from the respective standard curves in which the quantity or relative dilution of NucSeqI' or NucSeqII', expressed as copy number, is plotted on the X-axis.

28. The method of claim 24, wherein the concentration in the test sample in step (4) is the molar or weight concentration of NucSeqI or NucSeqII obtained from the respective standard curves in which the concentration or relative dilution of NucSeqI' or NucSeqII' is plotted on the X-axis.

* * * * *